(12) United States Patent
Cheung et al.

(10) Patent No.: US 8,906,318 B1
(45) Date of Patent: Dec. 9, 2014

(54) FEEDING-BOTTLE STERILIZER

(71) Applicant: Huiyang Allan Plastic & Electric Industries Co., Limited, Guangdong Province (CN)

(72) Inventors: Shu Sang Cheung, Guangdong Province (CN); To Yin Pang, Guangdong Province (CN)

(73) Assignee: Huiyang Allan Plastic & Electric Industries Co., Limited, Huizho (CN)

( * ) Notice: Subject to any disclaimer, the term of this patent is extended or adjusted under 35 U.S.C. 154(b) by 0 days.

(21) Appl. No.: 14/078,565

(22) Filed: Nov. 13, 2013

(30) Foreign Application Priority Data

Aug. 20, 2013 (CN) .......................... 2013 1 0362556

(51) Int. Cl.
*A61L 2/07* (2006.01)
*A61L 2/20* (2006.01)

(52) U.S. Cl.
CPC ....................................... *A61L 2/20* (2013.01)
USPC ......................................................... 422/292

(58) Field of Classification Search
USPC ......................................................... 422/292
See application file for complete search history.

(56) References Cited

U.S. PATENT DOCUMENTS 4,544,529 A * 10/1985 Hoeck ............................ 422/303
5,690,852 A * 11/1997 Saito et al. ..................... 219/725

FOREIGN PATENT DOCUMENTS

GB         2378901      *  2/2003

* cited by examiner

*Primary Examiner* — Sean E Conley
(74) *Attorney, Agent, or Firm* — Global IP Services, PLLC

(57) ABSTRACT

The present invention discloses a feeding-bottle sterilizer, comprising an upper cap, a base, and a container in which a feeding-bottle holder is placed, wherein an upper basket is arranged between the container and the upper cap, a baffle is arranged between the upper cap and the upper basket, a barrier is arranged between the base and the container, the baffle can slow down the steam flow out of the sterilizer, and a first, second, and third steam nozzle and a steam supply device are arranged on the base. The air cap of the first steam nozzle can rotate 360 degrees to ensure rapid and even steam distribution in space, the second steam nozzle stretches into the feeding bottle for sterilizing the feeding-bottle cavity, and the third steam nozzle extends into the upper basket. Furthermore, the feeding-bottle sterilizer has advantages of convenient cleaning, quick, and thorough sterilization.

7 Claims, 3 Drawing Sheets

FEEDING-BOTTLE STERILIZER

BACKGROUND OF THE INVENTION

The present invention relates to a sterilizer for a feeding-bottle, and more especially, to a feeding-bottle sterilize adopting the high-temperature steam sterilization.

People sterilize feeding bottles and nipples with boiling hot water generally, but this sterilization method is very complicated as it requires taking some time to boil water. Therefore, it takes a long time to complete the sterilization process. A feeding-bottle sterilizer currently appearing on the market heats and evaporates water into water vapor by a heating device and performs sterilization by the high-temperature water vapor in many forms. One is a container with simple structure, comprising a heating device and upper cap, but this kind of feeding-bottle sterilizer forms a larger sterilization space and it takes a longer time to fill the entire sterilization space with steam, thus causing the problem of non-thorough sterilization due to short sterilization time. Another is "A Feeding-bottle Sterilizer" with the application number of 201220538298.8 which is provided with main and auxiliary steam jet bars, wherein the steam is sprayed into the sterilization chamber via the main steam jet bar to sterilize the nipple and outer wall of the feeding bottle, the nozzle is fixed on the main steam jet bar, therefore it is difficult to distribute the hot steam in the entire sterilization cavity within a short period of time; wherein the steam is sprayed into the feeding bottle via the auxiliary steam jet bar to directly sterilize the nipple and inner wall of the feeding bottle, the feeding bottle and nipple hang on the auxiliary steam jet bar for sterilization, the bottle and nipple are easy to shake due to an instable position. Furthermore, the sterilization is not thorough due to a contact point between the feeding bottle or the nipple and the auxiliary steam jet bar.

BRIEF SUMMARY OF THE INVENTION

To address the aforesaid technical problem, the present invention provides a feeding-bottle sterilizer which applies the high-temperature water vapor to sterilize the feeding bottle. This feeding-bottle sterilizer addresses technical problems below, such as incomplete feeding-bottle sterilization and long sterilization time.

To address the aforesaid technical problem, the present utility model is realized through the following technical solution: a feeding-bottle sterilizer, comprising an upper cap, a base and a steam supply device arranged on the base, wherein a feeding-bottle container is disposed between the upper cap and the base, a feeding-bottle holder is arranged in the container, an upper basket is arranged between the container and the upper cap, a baffle is coupled to the bottom end of the upper cap and arranged between the upper cap and the upper basket, a first rotatable steam nozzle, a second steam nozzle inserted in the feeding bottle, and a third steam nozzle providing steam to the upper basket are arranged on the base, wherein the third steam nozzle extends from the base a id connects with an airway tube on the side wall of the container and an air jet hole on the side wall of the upper basket in series.

Preferably, the first steam nozzle includes a nozzle at the upper end of which an air cap rotating 360° and a bearing coordinating with the air cap rotation are arranged, wherein the outer end of the bearing is inserted into the air cap and the inner end coupled with the nozzle.

Preferably, a barrier is arranged between the base and the container, on which a basin baffle wall used in conjunction with the first steam nozzle and another basin baffle wall used in conjunction with the second steam nozzle are arranged.

Preferably, a placing mesh is arranged at the bottom of the upper basket for placing a nipple, the air jet hole is integrated with the upper basket by injection.

Preferably, a placing hole for placing the feeding bottle upside down is arranged on the feeding-bottle holder to avoid the second steam nozzle contacting with the inner wall of the feeding bottle, the number of which is the same as that of the basin baffle wall and the second steam nozzle.

Preferably, the number of the basin baffle wall and the first steam nozzle is 1, the number of the basin baffle wall, the second steam nozzle and the placing hole is 6.

Preferably, the steam supply device includes a water tank arranged on one side of the base, a pump arranged on the lower bottom surface of the base, a heating body for heating the water body and a diverter valve for controlling the flow direction of hot steam.

The present utility model provides a feeding-bottle sterilizer, wherein the baffle can slow down the overflow of steam outside the sterilizer which can rapidly reach the sterilization temperature and shorten the sterilization time after operation: the air cap of the first steam nozzle can rotate 360 degrees to ensure the rapid and even steam distribution in a space, the second steam nozzle directly stretches into the cavity of the feeding bottle and the third steam nozzle directly extends into the upper basket. Under the coaction of three steam nozzles, it takes little time to fill the entire sterilization space with steam which can distributes evenly, making the feeding-bottle sterilization more rapidly and thoroughly; the feeding-bottle holder is so arranged that the second steam nozzle can stretch into the feeding-bottle cavity without contacting with the inner wall of the feeding bottle, thus reaching a better sterilization effect; the upper cap, baffle, upper basket, feeding-bottle holder, container and base are removable mounding structure, making the entire machine cleaned conveniently and thoroughly.

DETAILED DESCRIPTION OF THE INVENTION

The present invention is detailed in combination with the drawings below to facilitate the better understanding of the technical solution of the present invention for technicians skilled in this art.

Figure 1:
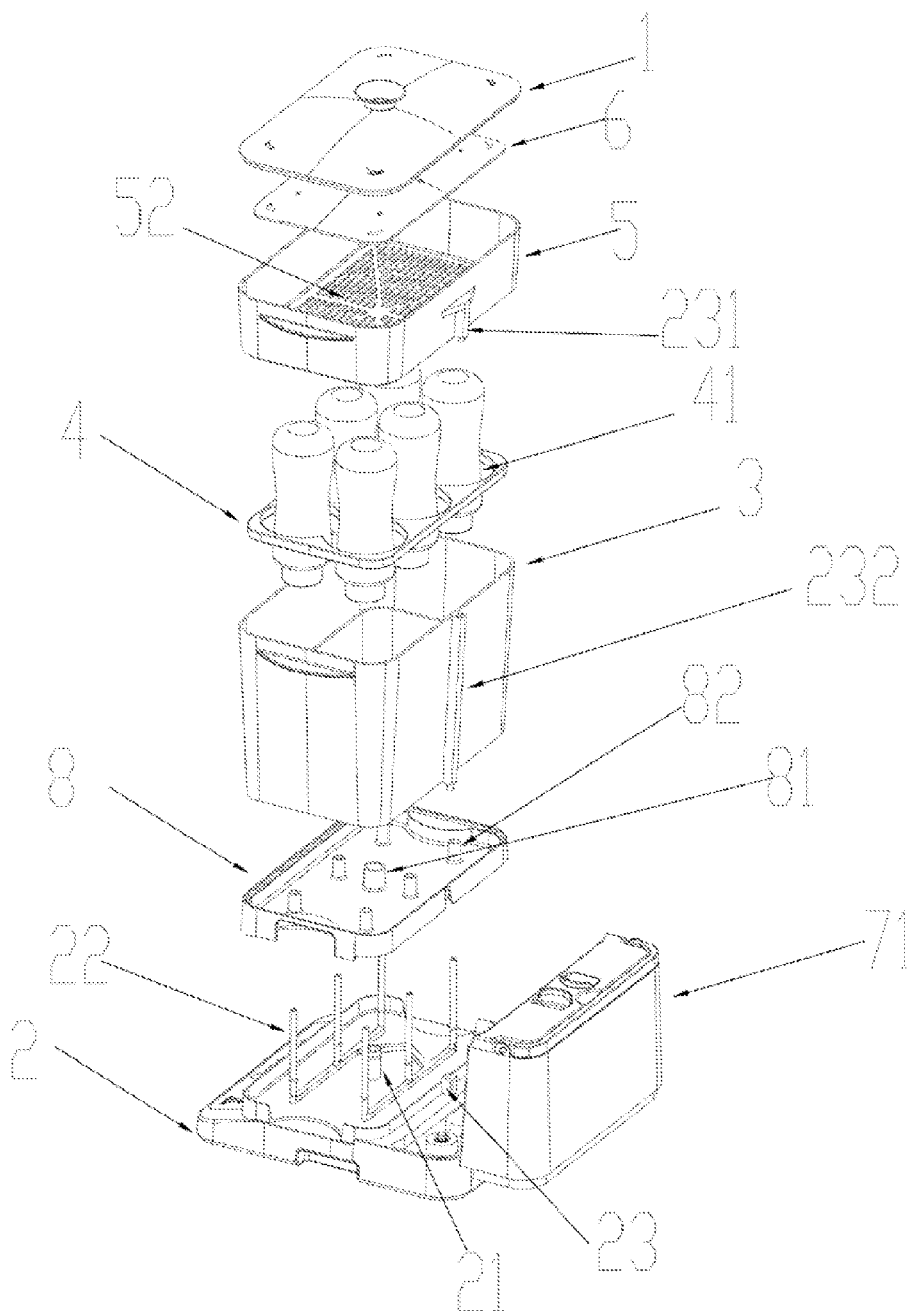
FIG. 1 shows the exploded view of the integrated structure according to the present invention.
Figure 2:
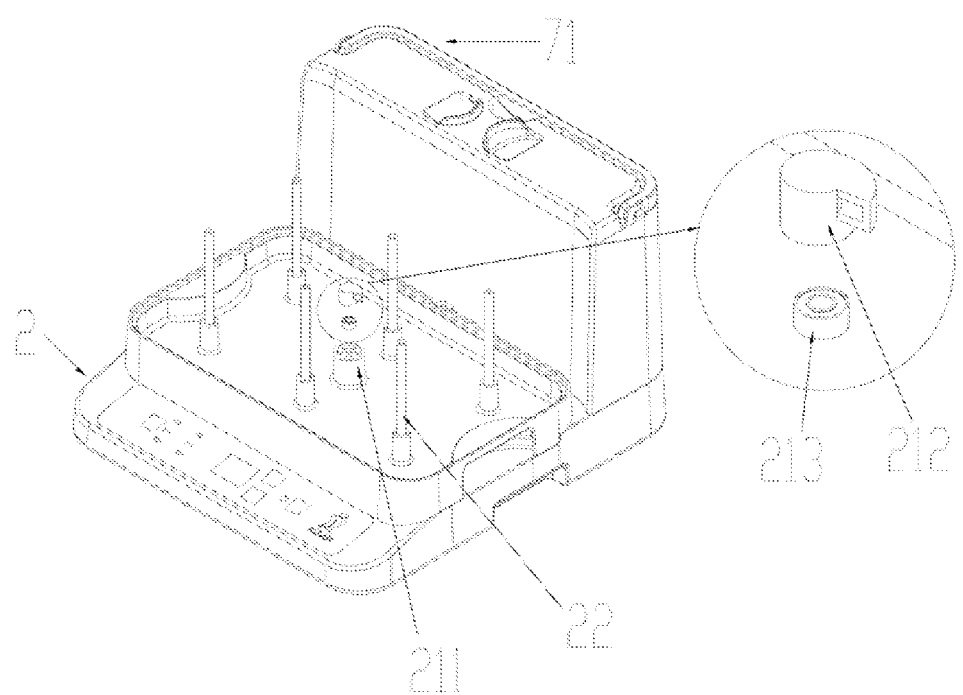
FIG. 2 shows the schematic view of the dimensional structure of the base according to the present invention.
Figure 3:
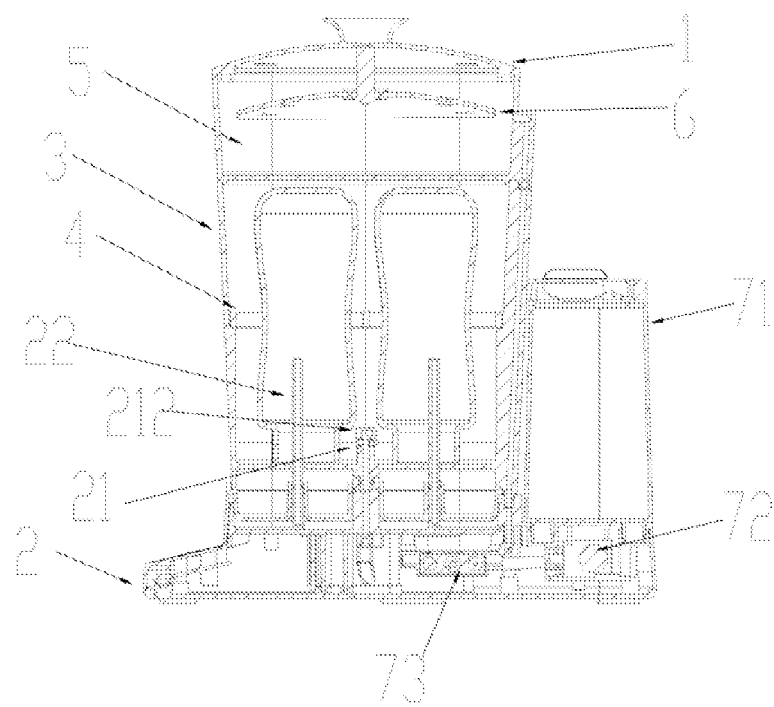
FIG. 3 shows the sectional schematic view according to the present invention.
Figure 4:
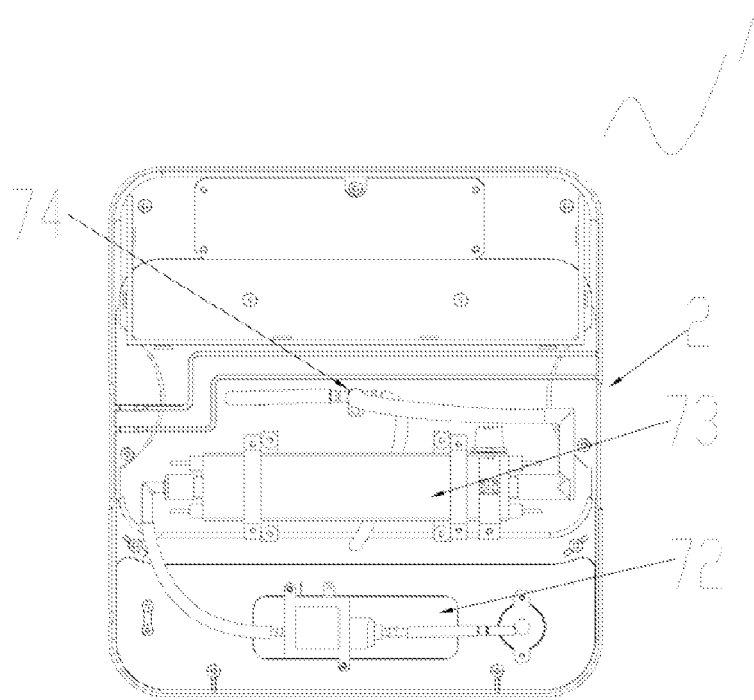
FIG. 4 shows the schematic view of the steam supply device arranged on the lower bottom surface of the base according to the present invention.

As shown in FIGS. 1~4, the present invention discloses a feeding-bottle sterilizer, comprising an upper cap 1, a base 2 and a container 3 between the upper cap 1 and the base 2 for holding one or more feeding bottles to be sterilized, a removable feeding-bottle holder 4 is placed in the container 3, wherein one or more placing holes 41 for placing the one or more feeding bottles upside down are arranged on the feeding-bottle holder. An upper basket 5 is arranged between the container 3 and the upper cap 1 and is used mainly for holding a nipple, a placing mesh 52 allowing the steam passing through is arranged at the bottom of the upper basket and is used for placing a nipple, an air jet hole 231 is connected with the third steam nozzle 23 in series and arranged on the external side of the side wall, wherein the air jet hole 231 is integrated with the upper basket 5 by injection. A baffle 6 is arranged between the upper cap 1 and the upper basket 5, which is fixed at the bottom end of the upper cap 1 with an adhesive. A first rotatable steam nozzle 21 mainly for sterilizing the outer wall of the feeding bottle, one or more second steam nozzles 22 mainly for sterilizing the inner wall of the feeding bottle, a third steam nozzle 23 mainly for sterilizing the feeding bottle nipple, and a steam supply device 7 providing hot steam for sterilizing the feeding bottle are arranged on the base 2.

The first steam nozzle 21 includes a nozzle 211 at the upper end of which an air cap 212 rotating 360° and a bearing 213 coordinating with the air cap rotation are arranged, wherein the outer end of the bearing 213 is inserted into the air cap 212 and the inner end of the bearing 213 is coupled with the nozzle 211. A barrier 8 is arranged between the base 2 and the container 3, on which a first basin baffle wall 81 used in conjunction with the first steam nozzle 21 and one or more second basin baffle walls 82 used in conjunction with the one or more second steam nozzles 22 are arranged. The number of the first basin baffle wall 81 and the number of the first steam nozzle 21 are both 1; the number of the one or more placing holes 41, the number of the one or more basin baffle walls 82 and the number of the one or more second steam nozzles 22 are both 6. To sterilize the inner wall of the feeding bottle, place the feeding bottle upside down in the placing hole 41 with the mouth downward; each second steam nozzle 22 extends into the bottle cavity through a corresponding basin baffle wall 82. The feeding bottle is fixed; therefore, a length of each second steam nozzle 22 extending into the feeding bottle is less than the height of the feeding bottle. So that the second steam nozzle 22 won't contact with the inner wall of the feeding bottle to avoid the problem of incomplete inner sterilization. The arrangement of the baffle 6 and barrier 8 can reduce the leakage of hot steam. The third steam nozzle 23 extends from the base and connects with an airway tube 232 on the side wall of the container 3 and an air jet hole 231 on the side wall of the upper basket through the barrier 8 in series, feeding the hot steam into the upper basket. The steam supply device 7 includes a water tank 71 arranged on one side of the base, a pump 72 arranged on the lower bottom surface of the base, a heating body 73 for heating the water body and a diverter valve 74 for controlling the flow direction of hot steam, which are connected via pipes.

The upper cap 1, upper basket 5, container 3 and base 2 of the feeding-bottle sterilize can be removed and installed for convenient cleaning. The baffle 6 can be removed & connected with the upper cap 1 with an adhesive, and formed a cavity with the upper basket 5. Put small parts, such as nipples into the cavity for sterilization. The baffle 6 can block the steam, slow down the escaping of steam outside the sterilizer, thus shortening the time of the steam filling the entire cavity with the rapid increasing steam temperature. A placing mesh 52 is arranged at the inner bottom of the upper basket 5 for placing a nipple, wherein an air jet hole of the third steam nozzle 23 is arranged on the inner wall. The high temperature steam performs convection between the container 3 and the upper basket 5 via the placing mesh 52. The steam flowing out from the diverter valve 74 flows into the first, second and third steam nozzles 21, 22 and 23, wherein the bearing 213 on the first steam nozzle coordinates with the air cap 212, the air cap 212 undergoes the opposite reaction force of the steam and rotates 360° under the coaction of the bearing after being ejected from the air cap 212 outlet. The first steam nozzle 21 and the second steam nozzle 22 extend into the container 3 through the basin baffle wall, wherein the second steam nozzle 22 stretches into the feeding bottle and the basin baffle wall can prevent leakage.

Specific realization process: the pump 72 arranged at the bottom of the base 2 pumps the water on the water tank 71 to the heating body 73 via a pipe, the heating body 73 heats up, water flows into the diverter valve 74 after absorbing heat and becoming water vapor, and then the water vapor penetrates into the first steam nozzle 21, the second steam nozzle 22 and the third steam nozzle 23, wherein the first steam nozzle 21 stretches into the feeding bottle mainly for sterilizing the cavity of the feeding bottle, the second steam nozzle 22 stretching into the container 3 mainly for sterilizing the outer wall of the feeding bottle in the container 3, the third steam nozzle 23 stretching into the upper basket 5 mainly for sterilizing the nipple on the upper basket 5 or other objects. The steam ejected from the first steam nozzle 82 applies an opposite force on the air cap 212 after being ejected via the air cap 212, wherein the air cap 212 rotates 360° under the action. Therefore, the steam can be distributed more evenly in the sterilization space. Furthermore, the baffle 6 can slow down the escaping of steam outside the sterilizer, thus shortening the time of the steam filling the entire sterilization space with the rapid increasing steam temperature. Therefore, it is more even and rapid to fill the entire sterilization space with steam with a better sterilization effect under the coaction of the first steam nozzle 21, the second steam nozzle 22, the third steam nozzle 23, baffle 6 and barrier 8.

The above described are preferred embodiments of the present invention. It should be noted that various changes and modifications made by those skilled in this art are within the protection scope of the claims of the present invention without departing from the spirit and essence of the present invention.

What is claimed is:

1. A feeding-bottle sterilizer, comprising an upper cap (1), a base (2) and a steam supply device (7) arranged on the base (2), wherein a feeding-bottle container (3) is disposed between the upper cap (1) and the base (2), characterized in that a feeding-bottle holder (4) is arranged in the container (3), an upper basket (5) is arranged between the container (3) and the upper cap (1), a baffle (6) is coupled to the bottom end of the upper cap (1) and arranged between the upper cap (1) and the upper basket (5), a first rotatable steam nozzle (21), one or more second steam nozzles (22) inserted in one or more feeding bottles to be sterilized and a third steam nozzle (23) providing steam to the upper basket are arranged on the base (2), wherein the third steam nozzle extends from the base and connects with an airway tube (232) on the side wall of the container (3) and an air jet hole (231) on the side wall of the upper basket (5) in series.

2. The feeding-bottle sterilizer according to claim 1, characterized in that the first steam nozzle (21) includes a nozzle (211) at the upper end of which an air cap (212) rotating 360° and a bearing (213) coordinating with the air cap rotation are arranged, wherein the outer end of the bearing (213) is inserted into the air cap (212) and the inner end of the bearing is coupled with the nozzle (211).

3. The feeding-bottle sterilizer according to claim 1, characterized in that a barrier (8) is arranged between the base (2) and the container (3), on which a first basin baffle wall (81) and one or more second basin baffle walls (82) are arranged; the first basin baffle wall (81) is used in conjunction with the first steam nozzle (21), and the one or more basin baffle walls (82) are used in conjunction with the one or more second steam nozzles respectively (22).

4. The feeding-bottle sterilizer according to claim 1, characterized in that a placing mesh (52) is arranged at the bottom of the upper basket for placing a nipple, and the air jet hole (231) is integrated with the upper basket (5) by injection.

5. The feeding-bottle sterilizer according to claim 1, characterized in that one or more placing holes (41) each for placing a feeding bottle upside down are arranged on the feeding-bottle holder (4) to avoid the one or more second steam nozzles (22) contacting the inner wall of the feeding bottles, the number of the one or more placing holes is the same as that of the one or more basin baffle walls (82) and is the same as that of the one or more second steam nozzles (22).

6. The feeding-bottle sterilizer according to claim 3, characterized in that the number of the basin baffle wall (81) and the number of the first steam nozzle (21) are both 1, the number of the one or more basin baffle walls (82), the number of the one or more second steam nozzles (22) and the number of the one or more placing holes (41) are both 6.

7. The feeding-bottle sterilizer according to claim 1, characterized in that the steam supply device (7) includes a water tank (71) arranged on one side of the base, a pump (72) arranged on the lower bottom surface of the base, a heating body (73) for heating the water body and a diverter valve (74) for controlling the flow direction of hot steam.

* * * * *